United States Patent
Bradley et al.

(10) Patent No.: US 10,349,799 B2
(45) Date of Patent: Jul. 16, 2019

(54) CLEANSING ARTICLE HAVING PRINTED TEXTURE

(71) Applicant: Kimberly-Clark Worldwide, Inc., Neenah, WI (US)

(72) Inventors: Elizabeth Oriel Bradley, Neenah, WI (US); Kevin Christopher Possell, Middleton, WI (US); James Michael Hoying, Marietta, GA (US); Melanie Samantha Chu, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 15/745,869

(22) PCT Filed: Jun. 15, 2017

(86) PCT No.: PCT/US2017/037671
§ 371 (c)(1),
(2) Date: Jan. 18, 2018

(87) PCT Pub. No.: WO2018/063458
PCT Pub. Date: Apr. 5, 2018

(65) Prior Publication Data
US 2018/0360288 A1 Dec. 20, 2018

Related U.S. Application Data

(60) Provisional application No. 62/402,350, filed on Sep. 30, 2016.

(51) Int. Cl.
*A47L 13/16* (2006.01)
*B08B 1/00* (2006.01)
(Continued)

(52) U.S. Cl.
CPC ............. *A47L 13/16* (2013.01); *A47K 7/02* (2013.01); *A47L 13/17* (2013.01); *A61K 8/0208* (2013.01);
(Continued)

(58) Field of Classification Search
CPC .......... A47L 13/00; A47L 13/10; A47L 13/16; A47L 13/17; A45D 2200/1018;
(Continued)

(56) References Cited

U.S. PATENT DOCUMENTS

| 271,075 A | 1/1883 | Jenks |
| D99,347 S | 4/1936 | De Pury |

(Continued)

FOREIGN PATENT DOCUMENTS

| EP | 0 405 043 B1 | 5/1994 |
| FR | 2 998 146 B1 | 10/2015 |
| WO | WO 1999/046119 A1 | 9/1999 |

OTHER PUBLICATIONS

Co-pending U.S. Appl. No. 15/745,857, filed Jan. 18, 2018, by Possell et al. for "Textured Cleansing Article."

(Continued)

*Primary Examiner* — Mark Spisich
(74) *Attorney, Agent, or Firm* — Kimberly-Clark Worldwide, Inc.

(57) ABSTRACT

The present invention relates to cleansing articles comprising first and second members forming the first and second outer surface of the article respectively, where the coefficient of friction and/or permeability of the members are different. In certain embodiments the first member comprises a plurality of polymeric protuberances and the second member comprises a plurality of hollow projections.

6 Claims, 5 Drawing Sheets

(51) Int. Cl.
*A47K 7/02* (2006.01)
*B32B 5/02* (2006.01)
*B32B 5/24* (2006.01)
*B32B 5/06* (2006.01)
*A61Q 19/10* (2006.01)
*A61K 8/02* (2006.01)
*A47L 13/17* (2006.01)

(52) U.S. Cl.
CPC .............. *A61Q 19/10* (2013.01); *B08B 1/006* (2013.01); *B32B 5/02* (2013.01); *B32B 5/06* (2013.01); *B32B 5/24* (2013.01); *A45D 2200/1018* (2013.01); *A45D 2200/1054* (2013.01); *A45D 2200/1063* (2013.01)

(58) Field of Classification Search
CPC .... A45D 2200/1054; A45D 2200/1063; B08B 1/003; B08B 1/006; A47K 7/00; A47K 7/02; A47K 7/03; A47K 10/00; A47K 10/02; A47K 10/16; B32B 3/00; B32B 5/02; B32B 5/022; B32B 5/06; B32B 5/24; B32B 2432/00
USPC .......... 15/104.93, 208, 209.1, 244.3; 428/92, 428/156, 196
See application file for complete search history.

(56) References Cited

U.S. PATENT DOCUMENTS

| | | | |
|---|---|---|---|
| 3,575,764 A | 4/1971 | McFarren | |
| D239,566 S | 4/1976 | Vogt | |
| 4,372,867 A | 2/1983 | Taragos | |
| 4,668,566 A | 5/1987 | Braun | |
| 4,741,941 A | 5/1988 | Englebert et al. | |
| 4,781,966 A * | 11/1988 | Taylor | A61F 13/49007 428/152 |
| 5,055,216 A | 10/1991 | Johnson | |
| D384,210 S | 9/1997 | Lefebvre du Grosriez | |
| 5,723,200 A | 3/1998 | Oshima et al. | |
| 5,744,149 A | 4/1998 | Girardot | |
| D451,682 S | 12/2001 | Jahner et al. | |
| D461,317 S | 8/2002 | Jahner et al. | |
| 6,461,720 B1 | 10/2002 | Graff | |
| D465,093 S | 11/2002 | Jahner et al. | |
| D465,338 S | 11/2002 | Jahner et al. | |
| 6,491,937 B1 | 12/2002 | Slavtcheff et al. | |
| 6,495,151 B2 | 12/2002 | McAtee et al. | |
| 6,810,554 B2 | 11/2004 | McKay | |
| 6,887,486 B2 | 5/2005 | Gregoire | |
| 6,998,360 B1 | 2/2006 | Picard | |
| D556,967 S | 12/2007 | Martins et al. | |
| 7,488,697 B2 | 2/2009 | Louis et al. | |
| 7,614,812 B2 | 11/2009 | Reddy et al. | |
| 7,629,043 B2 | 12/2009 | Lindsay et al. | |
| D651,411 S | 1/2012 | Wahlquist et al. | |
| D691,743 S | 10/2013 | Meyers | |
| D693,129 S | 11/2013 | Berenstain et al. | |
| D695,023 S | 12/2013 | Olson et al. | |
| D700,369 S | 2/2014 | Meyers | |
| 8,914,936 B2 | 12/2014 | Jemsby et al. | |
| 9,259,075 B2 | 2/2016 | Gordon et al. | |
| 9,327,473 B2 | 5/2016 | Finn et al. | |
| 9,352,531 B2 | 5/2016 | Berns et al. | |
| D774,784 S | 12/2016 | Chaffee et al. | |
| D800,458 S | 10/2017 | Nelson | |
| D821,103 S | 6/2018 | Delaney et al. | |
| D838,502 S | 1/2019 | Nelson | |
| 2001/0029967 A1 | 10/2001 | McDonough | |
| 2002/0087167 A1 | 7/2002 | Winitsky | |
| 2002/0146956 A1 | 10/2002 | Ngai | |
| 2003/0021953 A1 | 1/2003 | Graff | |
| 2003/0104750 A1 | 6/2003 | Kelly | |
| 2003/0217516 A1 | 11/2003 | Smith | |
| 2003/0228352 A1 | 12/2003 | Hasenoehrl et al. | |
| 2005/0067089 A1 | 3/2005 | Graff et al. | |
| 2006/0105143 A1 * | 5/2006 | Darnella Dorsey | A47L 13/16 428/137 |
| 2007/0098768 A1 | 5/2007 | Close et al. | |
| 2008/0037131 A1 | 2/2008 | Steenblik et al. | |
| 2009/0068409 A1 | 3/2009 | Bret et al. | |
| 2009/0194244 A1 | 8/2009 | Harper et al. | |
| 2011/0081528 A1 | 4/2011 | Shannon et al. | |
| 2013/0198989 A1 | 8/2013 | Jemsby et al. | |
| 2013/0330486 A1 | 12/2013 | Shields | |
| 2015/0047138 A1 | 2/2015 | Hughes | |
| 2015/0089761 A1 | 4/2015 | Boon et al. | |
| 2015/0202144 A1 | 7/2015 | Bodea | |
| 2015/0223661 A1 | 8/2015 | Metzger | |
| 2016/0174777 A1 * | 6/2016 | Wang | A47K 10/16 442/57 |
| 2017/0051442 A1 * | 2/2017 | Endle | D04H 1/54 |
| 2018/0360288 A1 | 12/2018 | Bradley et al. | |

OTHER PUBLICATIONS

Kleenex Exfoliating Cushions, Internet web page "https://www.popsugar.com/beauty/photo-gallery/39444489/image/39569505/Kleenex-Exfoliating-Cushions", Jan. 15, 2016, 2 pages.

Olay Daily Clean 4-in-1 Water Activated Cleansing Cloths, Internet web page "https://www.amazon.com/Olay-Daily-Activated-Cleansing-Cloths/dp/B00479FP4Q", viewed and printed Jul. 18, 2016, 11 pages.

* cited by examiner

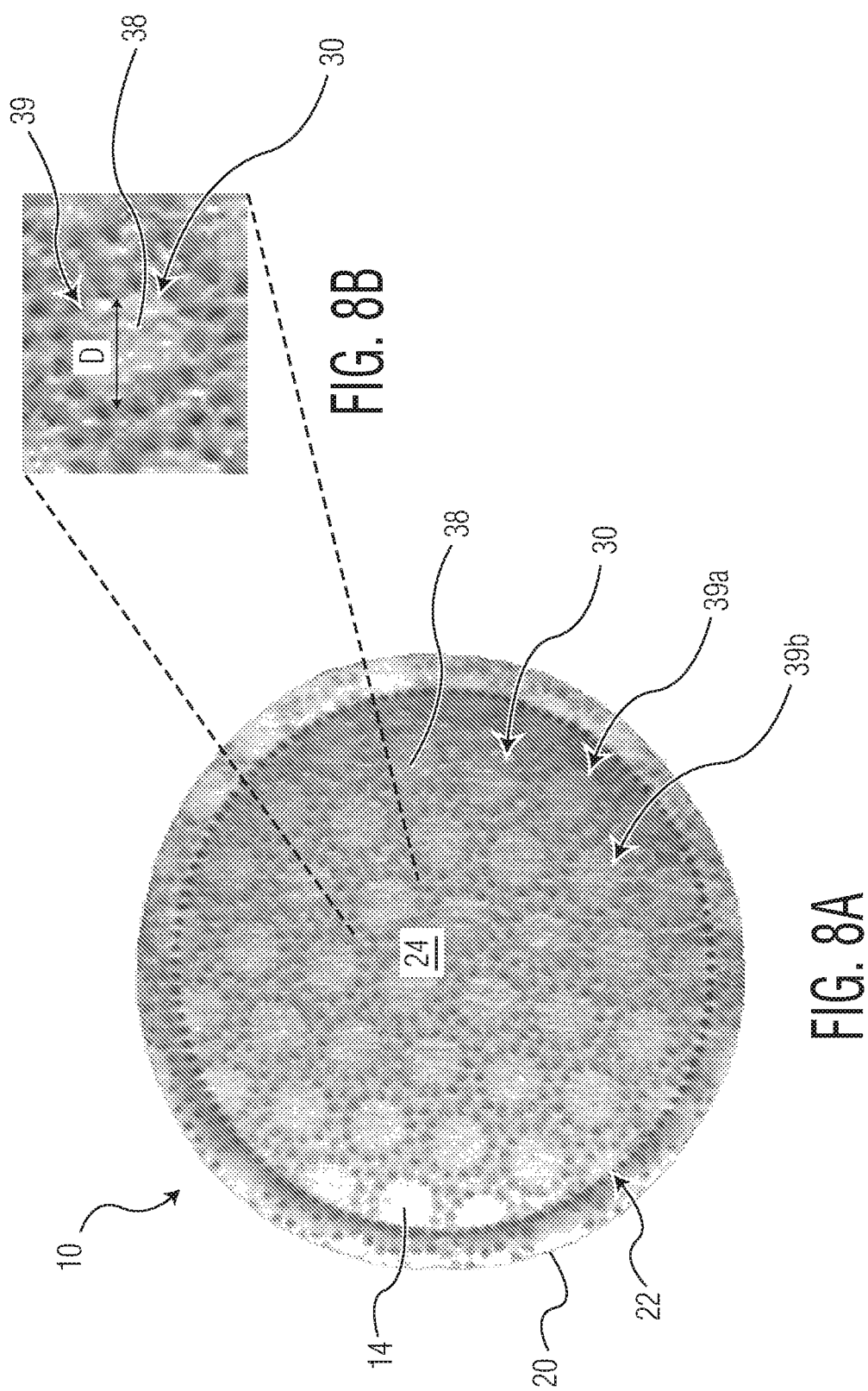

CLEANSING ARTICLE HAVING PRINTED TEXTURE

CROSS-REFERENCE TO PRIOR APPLICATIONS

This application is the U.S. National Phase application of International Application No. PCT/US17/37671 filed on Jun. 15, 2017, which claims the benefit of U.S. Provisional Patent Application No. 62/402,350, filed on Sep. 30, 2016.

BACKGROUND OF THE DISCLOSURE

It is well known in the art to deliver cleansing products to a user with a single disposable pad. While the construction of such disposable cleansing articles varies widely, it is common for cleansing articles to have a single layer having a single textured surface. For example, U.S. Pat. Nos. 3,537,121 and 3,910,284 disclose single layer nonwoven cleansing articles that clean without scratching or abrading the target surface. In other instances cleansing articles having two or more layers have been developed to improve the durability or hand feel of the pad. In certain instances the use of multiple layers may also enable a pad to have two wiping surfaces with differing textures. Too often however the texture provided by the different outer layers of the pad have significantly differing texture, such as one surface that is substantially smooth for polishing, and the like, and the other having a large degree of texture for scrubbing, and the like. Moreover, the layers comprise similar webs where one web simply has a texturing agent disposed on its surface. In this manner the texture of the pad may differ between the first and second sides, but the permeability of the layers is substantially similar.

Thus, there remains a need in the art for a cleansing article, such as a wiping pad, having two outer layers constructed from different materials having different permeabilities where both sides have some degree of three-dimensional topography, but provide the user with two distinct textured wiping surfaces.

SUMMARY OF THE DISCLOSURE

The present cleansing article overcomes many of the limitations of the prior art by providing a cleansing article having two distinct textures on its first and second sides. The dual textured cleansing articles of the instant invention allow for one side to be used for scrubbing and the other for gentle cleansing. Additionally, the more highly textured side of the article comprises raised polymeric elements that tend to concentrate removed soil and dirt on the raised areas, thereby enhancing the user's perception of cleansing efficacy.

Accordingly, in one embodiment the present invention provides a cleansing article comprising: a first member comprising a nonwoven web having a first and a second side and a plurality of polymeric protuberances disposed on the first side thereof, the first side forming the first outer surface of the cleansing article; a second member comprising a nonwoven web having a first and a second side, the second side forming the second outer surface of the cleansing article, wherein the first outer surface has a coefficient of friction greater than 0.50 and the second side has a coefficient of friction less than 0.50.

In another embodiment the invention provides a cleansing article comprising: a first member comprising a nonwoven web having a first and a second side and a plurality of polymeric protuberance disposed on the first side thereof, the first side forming the first outer surface of the cleansing article; a second member comprising a nonwoven web having a first and a second side, the first side having a plurality of projections substantially surrounded by a landing, the land areas lying in a first plane and the projections terminating at distal ends lying in a second plane, the first and second planes spaced apart a vertical distance from about 0.50 to about 1.50 mm, wherein the first side forms the second outer surface of the cleansing article; and a core, wherein the first outer surface has a coefficient of friction greater than 0.50 and the second outer surface has a coefficient of friction less than 0.50.

In still other embodiments the present invention provides a textured cleansing article having a first and a second side, the article comprising a first member comprising a nonwoven web having a first and a second side, the web having a permeability of 500 cfm or greater and the first side forming the first side of the article; a second member comprising a nonwoven web having a first and a second side, the web having a permeability less than 500 cfm and the first side forming the second side of the article; and a core, wherein the first side of the article has a coefficient of friction greater than 0.50 and the second side has a coefficient of friction less than 0.50.

In yet other embodiments the present invention provides a method of manufacturing a textured cleansing article comprising the steps of: (a) providing a first nonwoven web, (b) printing an ink comprising a heat-expandable microsphere on the first nonwoven web in a non-random pattern, (c) heating the printed nonwoven web at a temperature of at least about 120° C. to form a plurality of polymeric protuberances having an average height greater than about 250 µm, (d) providing a core comprising a porous open cell foam, (e) providing a second nonwoven web comprising a fluid-entangled laminate web having an outer and an inner surface, the outer surface of the web having a plurality of hollow projections, (f) plying the printed nonwoven web, the core and the second nonwoven web together, and (g) bonding the printed nonwoven web, the core and the second nonwoven web together.

BRIEF DESCRIPTION OF DRAWINGS

FIG. 8A is a top plane view of one surface of a textured cleansing article according to yet another embodiment of the present invention; and FIG. 8B is a detailed top plane view of one surface of a textured cleansing article,

DEFINITIONS

Figure 1:
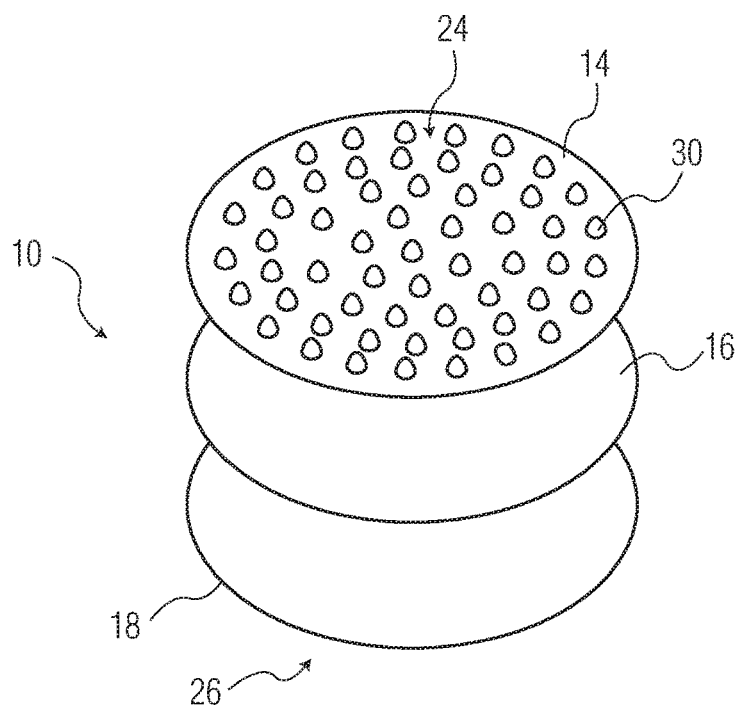
FIG. 1 is an exploded view of a textured cleansing article according one embodiment of the present invention.

As used herein the term "nonwoven web" generally refers to an article or sheet having a structure of individual fiber or fibers, which are interlard, but not in an identifiable manner as in a knitted fabric. Nonwoven fabrics or webs have been formed from many processes such as for example, meltblowing processes, air-laying processes, and bonded carded web processes.

As used herein the terms "meltblowing" and "meltblown process" generally refer to a method for forming a nonwoven fibrous web by extruding a molten fiber-forming material through a plurality of orifices in a die to form fibers while contacting the fibers with air or other attenuating fluid to attenuate the fiber into fibers, and thereafter collecting the attenuated fibers. An exemplary meltblowing process is taught in, for example, U.S. Pat. No. 6,607,624, As used herein the terms "spun-bonding" and "spun bond process" generally refer to a method for forming a nonwoven fibrous web by extruding molten fiber-forming material as continuous or semi-continuous fibers from a plurality of fine capillaries of a spinneret, and thereafter collecting the attenuated fibers. An exemplary spun-bonding process is disclosed in, for example, U.S. Pat. No. 3,802,817.

As used herein the terms "spun bond fibers" and "spunbonded fibers" generally refer to fibers made using spunbonding or a spun bond process. Such fibers are generally continuous fibers and are entangled or point bonded sufficiently to form a cohesive nonwoven fibrous web such that it is usually not possible to remove one complete spun bond fiber from a mass of such fibers.

As used herein the term "aft-laying" generally refers to a process by which a nonwoven fibrous web layer can be formed. In the air-laying process, bundles of small fibers having typical lengths ranging from about 3 to about 52 millimeters (mm) are separated and entrained in an air supply and then deposited onto a forming screen, usually with the assistance of a vacuum supply. The randomly oriented fibers may then be bonded to one another using, for example, thermal point bonding, autogenous bonding, hot air bonding, needle punching, calendering, a spray adhesive, and the like. An exemplary air-laying process is taught in, for example, U.S. Pat. No. 4,640,810.

As used herein the term "fluid-entangled laminate web" generally refers to a multi-layered nonwoven fibrous web comprising a support layer and a nonwoven projection web which are entangled using a fluid. An exemplary fluid-entangled laminate web and processes for forming the same are disclosed in, for example, U.S. Pat. No. 9,327,473.

As used herein, the term "fluid entangling" and "fluid-entangled" generally refers to a formation process for further increasing the degree of fiber entanglement within a given fibrous nonwoven web or between fibrous nonwoven webs and other materials so as to make the separation of the individual fibers and/or the layers more difficult as a result of the entanglement.

As used herein the term "co-form" or a "co-forming process" generally refer a process in which at least one fiber layer is formed substantially simultaneously with or in-line with formation of at least one different fiber layer. Webs produced by a co-forming process are generally referred to as "co-formed Webs."

As used herein the term "non-hollow" with particular reference to projections extending from a major surface of a nonwoven fibrous web means that the projections do not contain an internal cavity or void region other than the microscopic voids (i.e. void volume) between randomly oriented discrete fibers.

As used herein the term "hollow" with particular reference to projections extending from a major surface of a nonwoven fibrous web means that the projections contain an internal cavity or void region.

As used herein the term "layer" generally refers to a single stratum formed between two major surfaces. A layer may exist internally within a single web, e.g., a single stratum formed with multiple strata in a single web having first and second major surfaces defining the thickness of the web. A layer may also exist in a composite article comprising multiple webs, e.g., a single stratum in a first web having first and second major surfaces defining the thickness of the web, when that web is overlaid or underlaid by a second web having first and second major surfaces defining the thickness of the second web, in which case each of the first and second webs forms at least one layer. In addition, layers may simultaneously exist within a single web and between that web and one or more other webs, each web forming a layer.

As used herein the term "adjoining" with particular reference to various layers of the cleansing article of the present invention generally means a given layer (a first member) joined with or attached to another given layer (a second member), in a position wherein the first and second members are either next to (i.e., adjacent to) and directly contacting each other, or contiguous with each other but not in direct contact (i.e., there are one or more additional layers intervening between the first and second members).

As used herein the term "coefficient of friction" (COF) refers to the MIU value for a given sample as determined using a KES Surface Tester, as described in the Test Methods section below. Typically coefficient of friction is measured along one direction of a product. Where a product has both a machine and a cross-machine direction, coefficient of friction is measured in the machine direction (MD). Higher values of MIU indicate more drag on the sample surface. Coefficient of friction is generally referred to herein without reference to units. MIU is defined by:

$$MIU(\bar{\mu})=1/X\int_0^x \mu dx$$

where
$\mu$=friction force divided by compression force
$\bar{\mu}$=mean value of $\mu$
x=displacement of the probe on the surface of specimen, cm
X=maximum travel used in the calculation, 2 cm.

As used herein the term "surface smoothness" refers to the mean deviation of MIU (MMD) where higher values of MMD indicate more variation or less uniformity on the sample surface. The MMD value for a given sample as determined using a KES Surface Tester, as described in the Test Methods section below. Typically smoothness is measured along one direction of a product. Where a product has both a machine and a cross-machine direction, smoothness is measured in the machine direction (MD). Higher values of MMD indicate more drag on the sample surface. Surface smoothness is generally referred to herein without reference to units, MMD is defined as:

$$MMD=1/X\int_0^x |\mu-\bar{\mu}| dx$$

where
$\mu$=friction force divided by compression force
$\bar{\mu}$=mean value of $\mu$
x=displacement of the probe on the surface of specimen, cm
X=maximum travel used in the calculation, 2 cm.

As used herein the term "permeability" generally refers to the air permeability of a given layer of the cleansing article measured as described in the Test Methods section below.

The term "volume" when used herein in reference to dots or protuberances generally refers to the approximate average volume of protuberances having a partially spherical shape. Volume (V) is calculated from the measured dot radius (r) and dot height (h) as follows:

$$c = \sqrt{h(2r - h)}$$
$$V = \frac{\pi}{6}(3c^2 + h^2)$$

DETAILED DESCRIPTION OF THE DISCLOSURE

The present invention provides a textured cleansing article for use in cleaning any manner of body surfaces, and particularly a user's face. The textured cleansing article comprises first and second outer members forming first and second sides thereof. The first and second sides of the article are both textured, although preferably the sides have different textures to provide the user with differing degrees of cleaning in a single cleansing article. For example, in one embodiment the invention provides a cleansing article having a first side and a second side, the first side comprising a plurality of protuberances printed thereon and having a coefficient of friction greater than 0.50, more preferably greater than about 0.75 and still more preferably greater than about 1.00, such as from 0.50 to about 1.50 and more preferably from about 0.75 to about 1.20. Conversely the second side is substantially free from printed protuberances and generally has a coefficient of friction less than 0.50 and more preferably less than about 0.40, such as from about 0.20 to 0.50.

One embodiment of the instant cleansing article is illustrated in FIG. 1, which illustrates an article 10 comprising three layers—a first outer layer 14, a core 16 and a second outer layer 18. Generally each layer 14, 16, 18 is formed from a different material so as to provide the article 10 with first and second sides 24, 26 with different properties such as texture or permeability. Each of the layers have a periphery along the outer edges of the material circumscribing the piece of material forming the layer.

The layers 14, 16, 18 may be combined into a single article 10 by any standard adhesion method including, for example, embossing, thermal bonding, adhesive bonding, ultrasonic bonding, stitching, or combinations thereof. In one embodiment, such as that illustrated in FIG. 2, the layers are joined to one another by embossing to create a bonded edge 22 along the periphery 20 of the cleansing article 10.

The first and second sides of the article preferably have different textures, which are generally provided by the use of different materials to form the two outer layers. For example, with reference to the embodiment illustrated in FIG. 4, the first member 14 comprises a nonwoven web having a plurality of polymeric protuberances 30 disposed thereon and the second member 18 comprises a fluid-entangled laminate web having a plurality of projections 32 formed from the laminate web. The construction of the first member 14, including the nonwoven web and the polymeric material used to form the protuberances 30, may be designed such that the first side 24 has a coefficient of friction greater than 0.50, more preferably greater than about 0.75 and still more preferably greater than about 1.00, such as from 0.50 to about 1.50 and more preferably from about 0.75 to about 1.20. Conversely, the fluid-entangled laminate web forming the second outer layer 18 may be constructed such that the second side 26 generally has a coefficient of friction less than 0.50 and more preferably less than about 0.40, such as from about 0.20 to 0.50.

Thus, in certain embodiments the first and second sides 24, 26 have different coefficients of friction where the coefficient of friction of the first side 24 is greater than the coefficient of friction the second side 26, such as at least about 10 percent greater, and more preferably at least about 30 percent greater and still more preferably at least about 75 percent greater, such as from about 10 to about 125 percent greater and more preferably from about 30 to about 100 percent greater. For example, the first side 24 may have a coefficient of friction greater than about 0.75 and the second side 26 may have a coefficient of friction less than about 0.30.

In addition to providing the first and the second sides 24, 26 of the article 10 with different degrees of texture, the materials used to form the first and second members 14, 18 may be selected such that the first and the second sides 24, 26 have differing degrees of permeability. For example, in one embodiment, the first member 14 has a permeability of 500 cfm or greater, such as from 500 to about 700 cfm and more preferably from about 500 to about 600 cfm and still more preferably from about 525 to about 575 cfm. Conversely, the second outer member has a permeability less than 500 cfm, such as from about 300 to 500 cfm and more preferably from about 400 to about 475 cfm. In this manner the permeability of the first and the second sides 24, 26 differs such that when the core member 16 is designed to generate foam such as through the use of a resiliently-deformable porous material the foam is transmitted through the first and the second sides 24, 26 at differing degrees. As such, the article may have sides with differing degrees of texture and foaming to provide the user with two distinct cleansing experiences.

With reference again to FIG. 1 in certain embodiments the cleansing article 10 may have a circular shape, however, the invention is not so limited. The size of the article may be shaped and/or sized to provide sufficient surface area to enable a user to clean and/or treat the intended body part(s). By way of example, for many personal care applications it will be adequate for the article to have a maximum dimension from about 3 to about 20 cm. such as from about 4 to about 12 cm and more preferably from about 5 to about 10 cm. The shape of the article 10 may vary as desired and may comprise rectilinear, curvilinear and irregular shapes. By way of example, the article may be circular, elliptical, oval, square, rectangular, and so forth. In one embodiment the article has a generally square perimeter with rounded corners with approximately equal lengths and widths, which may be from about 5 to about 15 cm and more preferably from about 5 to about 10 cm. In other embodiments the article has a circular shape and a maximum diameter from about 5 to about 15 cm and more preferably from about 5 to about 10 cm.

Figure 2:
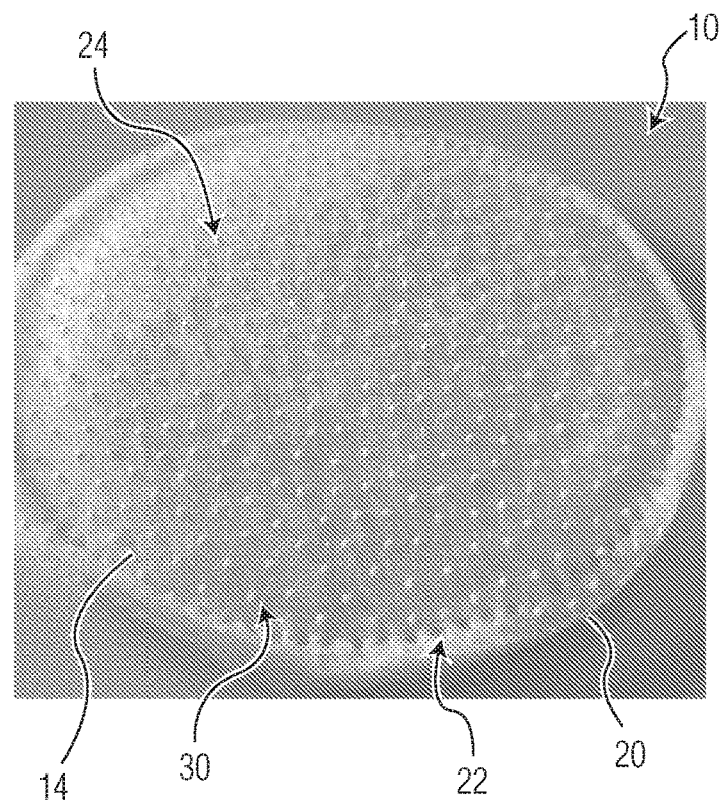
FIG. 2 is a top plane view of one surface of a textured cleansing article according to one embodiment of the present invention.

Turning now to FIG. 2, one embodiment of a first outer member 14 of the article 10 is illustrated. The first outer member may be made from any suitable synthetic or natural material so as to provide a layer that is compliant and compressible to the touch. The first outer member may be wet laid, air laid, or made by other methods. Numerous materials are suitable for use in the first outer member and include, but are not limited to, knit or woven fabrics, nonwoven fabrics, and porous open cell foams. Suitable polymers include, but are not limited to, polyolefins (e.g. polyethylene and polypropylene), polyesters (e.g. polyethylene terephthalate), polyamides (e.g. nylon), viscose, and mixtures thereof. Desirably, the first outer member comprises a fibrous layer having a substantially uniform composition and is laid in such a manner so as to provide a substantially uniform outer surface. Non-limiting examples of suitable natural materials and derivatives thereof include woven and nonwoven materials made of fibers such as cotton, wood pulp, viscose or mixtures thereof. Exemplary nonwoven fabrics include, but are not limited to, spunlace (hydroentangled materials), spunbond, meltblown, and bonded-carded webs.

The first outer member may have a basis weight from about 10 to about 200 grams per square meter (gsm), such as from about 30 to about 150 gsm, and still more preferably from about 50 to about 100 gsm. By way of a specific example, the first outer member may comprise a bonded carded web having a basis weight from about 30 to about 100 gsm. The foregoing webs may have a permeability of 500 cfm or greater, such as from 500 to about 600 cfm and more preferably from 500 to about 550 cfm.

The first outer member generally comprises a plurality of protuberances, also referred to herein as nodules, protrusions or dots, printed on the outer surface thereof. With reference to FIG. 2, a plurality of polymeric protuberances 30 are disposed on the outer surface of the first member 14 to provide the first side 24 of the article 10 with texture. Generally the protuberances are raised above the outer surface of the web forming the first layer. Together the protuberances 30 and the web 14 form the first surface 24 of the article 10.

The protuberances may take any number of different shapes, such as circular, oval, square, or the like. In certain instances, protuberances may be referred to herein as "dots," regardless of their actual shape, it being understood that the definition encompasses any shape and form of the protuberances. In a particularly preferred embodiment the protuberances have a partially spherical shape.

In certain embodiments the protuberances have a spherical or a partially spherical shape and an average diameter, generally measured at the point the protuberance contacts the web, of at least about 500 μm and more preferably at least about 700 μm and still more preferably at least about 1,000 μm, such as from about 500 to about 2,000 μm and more desirably from about 700 to about 1,500 μm.

The protuberances generally extend from the surface plane of the first side in the z-direction providing the protuberances with a height. The average height of the protuberances is generally greater than about 150 μm, more preferably greater than about 250 μm, and still more preferably greater than about 400 μm, such as from about 150 to about 750 μm and more preferably from about 300 to about 650 μm. The average height of the protuberances is generally measured using the image analysis technique described in the Test Methods section below. In certain preferred embodiments the height of the protuberances is relatively uniform such that the standard deviation of height is less than about ±50 μm and more preferably less than about ±25 μm.

In a particularly preferred embodiment the protuberances are spherical or partially spherical and have a volume greater than about 0.50 mm$^3$ and more preferably greater than about 0.55 mm$^3$ and still more preferably greater than about 0.60 mm$^3$, such as from about 0.50 to about 0.75 mm$^3$ and more preferably from about 0.55 to about 0.70 mm$^3$. In other embodiments the protuberances have a spherical or a partially spherical shape, an average height greater than about 500 μm, such as from about 500 to about 1,000 μm, and a volume greater than about 0.50 mm$^3$ such as from about 0.50 to about 0.75 mm$^3$.

The protuberances may be applied to the first outer layer in a random or non-random pattern. In a preferred embodiment the protuberances are applied to the first outer layer in a non-random pattern and cover at least about 5.0 percent of the surface area of the outer layer, such as from about 5.0 to about 15.0 percent. In other embodiments the protuberances may cover at least about 7.0 percent of the surface of the first outer layer, and still more preferably at least about 9.0 percent, such as from about 7.0 to about 13.0 percent. In other embodiments the number of protuberances per unit area of the first outer layer is generally greater than about 100,000 protuberances/m$^2$ and still more preferably greater than about 120,000 protuberances/m$^2$, such as from about 100,000 to about 200,000 protuberances/m$^2$ and more preferably from about 120,000 to about 170,000 protuberances/m$^2$.

The protuberances may be applied in any number of different non-random patterns including, for example, the non-random patterns illustrated in FIGS. 5-8A. The pattern is generally formed by protuberances 30 printed on the first outer member 14 which forms first side 24 of the article 10. The article 10 may have a bonded edge 22 adjacent to its outer peripheral edge 20, which may lend aesthetics to the article 10, but generally does not form part of the overall pattern.

Figure 7:
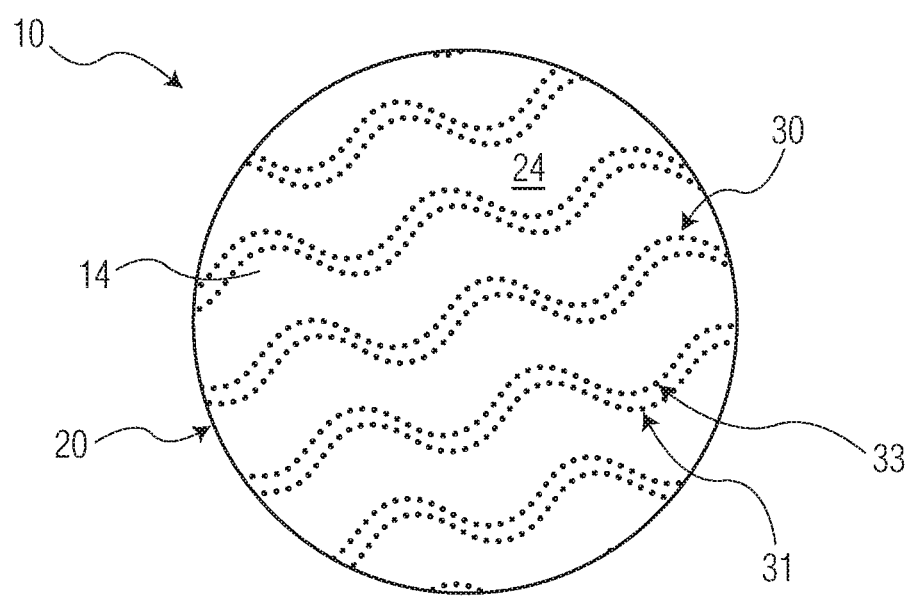
FIG. 7 is a top plane view of one surface of a textured cleansing article according to another embodiment of the present invention.

In certain embodiments, such as that illustrated in FIG. 7, the protuberances 30 may be disposed in a pattern comprising first 31 and second 33 paired lines having a wave form. In other embodiments, such as that illustrated in FIG. 8A, the protuberances 30 may be disposed in a pattern comprising a plurality of circles 39a, 39b, having an unprinted center 38. As illustrated in FIG. 8B, the unprinted center 38 may have a diameter (D), which in certain embodiments may be uniform amongst the plurality of circles forming the pattern. The protuberances 30 may form a circle 39 having a diameter (D) from about 5.00 to about 15.0 mm and more preferably from about 7.50 to about 10.00 mm. In certain embodiments the circles 39 forming the pattern may comprise from about 10 to about 15 protuberances 30 per circle.

The protuberances may be formed by depositing an ink, also referred to herein as a paste, upon a preformed web. Inks suitable to be used in the present invention are generally water based inks comprising an expandable microsphere and more preferably a heat-expandable microsphere, also referred to herein as an active agent. Heat-expandable microspheres are well known in the art and preferably comprise a thermoplastic polymer shell encapsulating a propellant. The propellant is preferably a liquid having a boiling temperature not higher than the softening temperature of the thermoplastic polymer shell. Upon heating of microspheres the propellant increases the internal pressure at the same time as the shell softens causing the microspheres to expand and increase in size, In certain embodiments protuberances may be formed by printing an ink composition comprising heat-expandable microspheres, a film-forming polymeric binder and optionally a rheology modifier; a surface tension modifier, a colorant, an inorganic filler and water. Suitable inks may comprise from about 15 to about 45 percent, by weight of the ink, solid material. The heat-expandable microspheres may have a diameter in the unexpanded state from about 5 to about 100 μm and more preferably from about 10 to about 50 µm. Suitable heat-expandable microspheres are commercially available under the trade name Expancel™ (Akzo Nobel).

The protuberances are preferably printed on the web in one or more patterns using rotogravure or gravure printing (direct or indirect), flexographic printing, screen printing, stencil application, and so forth. Generally the process of creating one or more protuberances on the surface of a web will be referred to herein as "printing", it being understood that the term is not limited to any particular process or apparatus. In one embodiment, printing of the paste formulation on the web is performed by using a conventional rotary screen printer, such as those commercially available from SPGPrints America Inc., Charlotte, N.C. Printing may be carried out during manufacture of the web or in a separate off-line process. The web may be wet when printed or it may be dry.

Generally, after the paste is printed the web is heated. The printed web may be heated by a dryer oven, which should be sufficiently hot to dry the web and to activate the paste to achieve the desired protuberance shape, such as by heating the web to a temperature of at least about 120° C. In other embodiments the web may be heated in two or more stages having different temperatures to dry the web and activate the paste. For example, the web may be subjected to a first drying stage having a temperature from about 110 to about 120° C. followed by a second stage having a temperature from about 140 to about 150° C. Regardless of whether the web is heated in a single or multiple stages, the web is exposed to a sufficient temperature for a sufficient amount of time to dry the web and allow activation of the paste. After leaving the dryer the printed web may be rolled and slit to size for use in forming the textured article according to the present invention.

Providing the first side of the article with a printed pattern as described above generally provides the first side with improved texture compared to the first side of commercially available cleansing articles (the first side of the articles being the side comprising polymeric protuberances). For example, as set forth in Table 1, below, the inventive articles generally have a coefficient of friction about 100 percent greater than commercially available cleansing articles.

plane. The height of the projections may vary, but generally projections are of similar height and define a second plane lying above the first plane.

The second outer member is generally coextensive with the first outer member and disposed opposite thereto, but generally not immediately adjacent to the first outer member. In certain embodiments a core layer, which will be discussed in more detail below, may be disposed between the first and second outer members. While the second outer member is generally of similar shape and size to the first outer member, the second outer member generally comprises a different material than the first outer member and has distinctly different degrees of coarseness and/or hand-feel in order to provide still further skin treatment options and/or tactile sensations for the user. Further, it is generally preferred that the second outer member comprise a material having a different permeability than the first outer member. In particularly preferred embodiments the first outer member has a higher coefficient of friction and lower permeability compared to the second outer member.

In certain embodiments, the second outer member may comprise a fibrous material such as a nonwoven web, which in certain instances may comprise a laminate of two or more webs. For example, the second outer member may comprise a multilayered laminated web comprising spunbonded/meltblown/spunbonded laminate, a spunbonded/meltblown laminate, and the like.

Preferably the outer surface of the second outer member has a three dimensional shape to provide a texturized surface. A texturized surface is particularly useful when the cleansing article is used to scrub or clean surfaces, such as the skin. In one embodiment the second outer member comprises a single ply nonwoven web, the second outer member having a top and a bottom surface where the top surface is texturized. The manner in which a texturized surface is formed on a nonwoven web for use on the second outer member can vary depending upon the particular application of the desired result. For example, the precursor web may be embossed to provide a texturized surface. In another embodiment the web may be matte finished to provide a texture. In yet other embodiments a texturized surface may be imparted by thermally point unbonding a nonwoven web

TABLE 1

| Article | % Printed Area | Dot Spacing (mm) | Dot Diameter (mm) | Average Dot Height (µm) | Approx. Dot Volume (mm³) | Coefficient of Friction | Surface Smoothness |
|---|---|---|---|---|---|---|---|
| Inventive 1 | 10.4 | 1.6 | 0.94 | 611 | 0.51 | 1.089 | 0.059 |
| Inventive 2 | 12.7 | 1.6 | 1.2 | 507 | 0.69 | 0.680 | 0.054 |
| Publix Cleansing Towelettes, Exfoliating | 3.6 | 3.9 | 0.74 | 129 | 0.13 | 0.250 | 0.020 |
| CVS Exfoliating Cleansing Wipes | 4.5 | 3 | 0.73 | 261 | 0.23 | 0.266 | 0.013 |
| Olay Fresh Effects Clear Skin Wet Clothes | 8.8 | 2.3 | 1.17 | 156 | 0.26 | 0.325 | 0.034 |
| Beauty 360 Exfoliating Dual-Action Facial Cloths | 11.6 | 0.97 | 0.68 | 96 | 0.09 | 0.197 | 0.016 |

Figure 3:
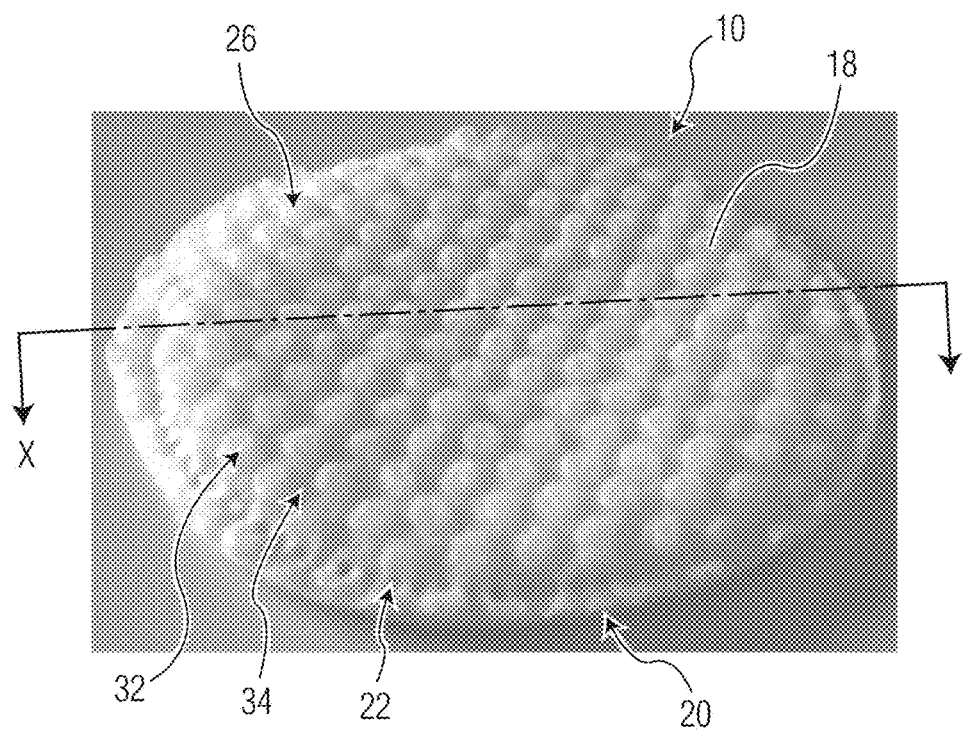
FIG. 3 is a top plane view of one surface of a textured cleansing article according to one embodiment of the present invention.

Opposite the first side 24 is a second side 26 of the article 10, one embodiment of which is illustrated in FIG. 3. The second side 26 is formed by a second member 18, such as a fluid-entangled laminate web having a plurality of projections 32. Interposed between projections 32 are land areas 34 lying in a first plane. Together the projections 32 and the land areas 34 form the second side 26 of the article 10. Generally the projections extend outwardly and away from the first plane and terminate at distal ends to define a second to form a plurality of tufts. As used herein, a substrate that has been "thermally point unbonded" refers to a substrate that includes raised unbonded areas or lightly bonded areas that are surrounded by bonded regions. For example, bumps or tufts are the unbonded or lightly bonded areas that form raised projections off the surface of the nonwoven web to provide the necessary texture. In still other embodiments the web may be fluid-entangled to form projections extending outwardly and away from the top surface of the web, such as described in U.S. Pat. No. 9,327,473.

Generally the means of texturizing the surface of the second outer member does not involve the deposition of material onto the surface of the web. Thus, in one preferred embodiment, the first and second outer members differ in the manner in which their outer surfaces are texturized. For example, the first outer member may be texturized by depositing a polymeric material on its outer surface to form protuberances while the second outer member may be texturized by mechanically treating the precursor web such as by embossing or fluid-entanglement to form projections.

In a particularly preferred embodiment the second outer member comprises a fluid-entangled laminate web with projections extending outwardly and away from at least one intended external surface of the laminate. Generally the fluid-entangled laminate web comprises a support layer and a fibrous nonwoven projection web where the fibers of the projection web cross the interface between the layers and are entangled with and engage the support layer so as to form the laminate. The basis weights for the fluid-entangled laminate web may vary depending on the end-use applications outlined herein, but generally may range from about 50 to about 200 gsm, though basis weights outside this range may be used depending upon the particular end-use application.

While the projections can be filled with fibers from the projection web and/or the support layer it is generally desirable for the projections to be generally hollow. The hollow projections desirably have closed ends which are devoid of holes or apertures. Such holes or apertures are to be distinguished from the normal interstitial fiber-to-fiber spacing commonly found in fibrous nonwoven webs. In some applications, however, it may be desirable to increase the pressure and/or dwell time of the impinging fluid jets in the entangling process as described below to create one or more holes or apertures (not shown) in one or more of the hollow projections. Such apertures may be formed in the ends or side walls of the projections as well as in both the ends and side walls of the projections.

The shape of the hollow projections may be, for example, round, oval, square, rectangular, triangular, diamond-shaped. In one preferred embodiment, the hollow projections may be round when viewed from above with somewhat domed or curved tops or ends such as seen when viewed in the cross-section. Both the width and depth of the hollow projections can be varied as can be the spacing and pattern of the projections. Further, various shapes, sizes and spacing of the projections can be utilized in the same web. In one embodiment, the projections can have a height from about 0.5 to about 10 mm, such as from about 0.5 to about 5 mm and more preferably from about 0.75 to about 1.5 mm.

The hollow projections in the laminate web are located on and emanate from the outer surface of the web. The hollow projections have open ends which are located towards the inner surface of the web and may be covered by the second surface of the support layer or web or the inner surface of the projection web, depending upon the amount of fiber that has been used from the projection web to form the projections. The projections are surrounded by land areas, which are also formed from the outer surface of the projection web, though the thickness of the land areas is comprised of both the projection web and the support layer. This land area may be relatively flat and planar or it may have topographical variability built into it. For example, the land areas may be provided with depressions which extend all or part way into the projection web and/or the support layer. In addition, the land areas may be subjected to embossing which can impart surface texture and other functional attributes to the land area. Still further, the land areas may be provided with apertures which extend through the laminate so as to further facilitate the movement of fluids (such as the foam exuded by the core layer) into and through the laminate.

In addition to the first and second outer members the article generally comprises one or more inner layers, such as a core member, to provide additional and/or enhanced functions. Thus, the article can be used to clean a user's skin, and particularly their face, by wetting the article and then rubbing one or both of the first and second sides against the same to achieve the desired level and type of cleaning.

Figure 4:
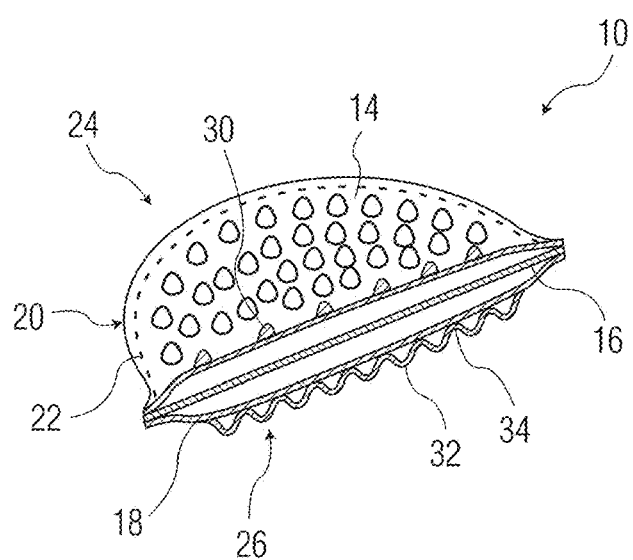
FIG. 4 is a cross-sectional view of a textured cleansing article according to one embodiment of the present invention through the line X-X of FIG. 3.
Figure 5:
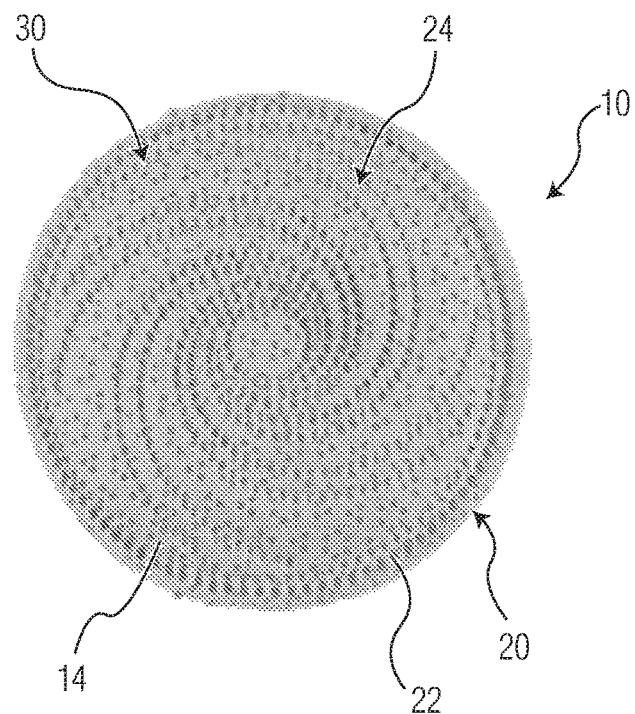
FIG. 5 is a top plane view of one surface of a textured cleansing article illustrating one exemplary pattern of protuberances disposed on one surface of the article.
Figure 6:
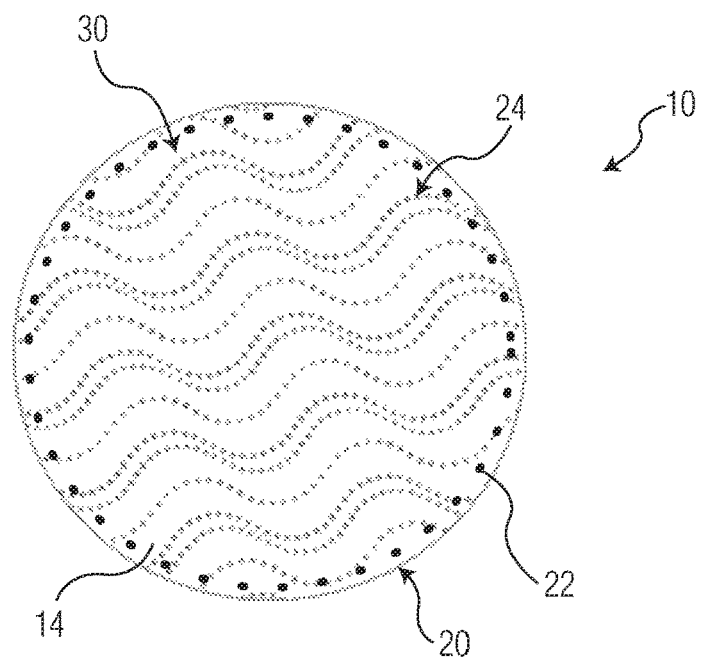
FIG. 6 is a top plane view of one surface of a textured cleansing article according to one embodiment of the present invention.

By way of example, and in reference to FIG. 4, the cleansing article 10 may optionally include a core member 16 to enhance the functionality of the cleansing article 10. In one aspect the core member 16 may be located between the first outer member 14 and second outer member 18. The core member 16 can comprise one or more different materials depending on the desired properties of the cleansing article 10. In one aspect, the core member 16 may provide or enhance the ability of the cleansing article 10 to generate foam such as through the use of a resiliently-deformable porous material. In this regard, the compression and expansion of the porous material works in combination with existing and/or applied cleanser to generate numerous bubbles and create a rich foam or lather. Highly porous, low density materials that are resiliently-deformable are well suited to providing such a function; suitable materials include, but are not limited to, through-air bonded nonwoven fabrics, porous or open cell foams, compressed viscose or cellulose, and so forth. By way of non-limiting example, materials capable of providing such a benefit include those described in U.S. Pat. Nos. 4,068,036, 5,985,434 and 7,358,282.

In a further aspect, the core member may be employed to improve the ease of handling the cleansing article such as by providing additional stability or bending stiffness to the cleansing article such that the article does not readily bend or fold onto itself under its own weight or the weight of any applied water or cleansers. The bending stiffness or stability of the article or core member can be increased by the use or addition of one or more supporting layers such as a scrim reinforcing material or by increasing the density or the degree of cross-linking or interstitial bonding within the materials comprising the core member. In this regard, the aforementioned materials suitable for foam generation may also be provided with relatively higher degrees of bonding or cross-linking in order to obtain the desired degree of bending stiffness and resiliency. The size and location of the core member will vary with the selected material and function. In many embodiments, it will be desirable for the core member to be centrally located within the article and to have a size that is smaller than that of the article itself such that the core member does not extend to the edge or form a part of any edge seal.

In yet a further aspect, the core member may be utilized to provide a visual or tactile cue to the user that the article is sufficiently wetted for use. By way of example, the core member may comprise one or more materials that significantly expand upon wetting such that the user can easily see or feel an increase in the volume of the article and thereby understand when the article if sufficiently wet and ready for use. In this regard, the core member may comprise a sealed packet or pouch containing highly water-swellable materials such as, for example, "superabsorbent" materials. Superabsorbent materials are well known and widely used in absorbent personal care articles such as diapers and other incontinence garments; non-limiting examples of which include alkali metal salts of polyacrylic acids, polyacrylamides, polyvinyl alcohol, ethylene maleic anhydride copolymers, polyvinyl ethers, hydroxypropyl cellulose, polyacrylates, modified starch such as hydrolyzed acrylonitrile grafted starch, and so forth. The swellable or superabsorbent materials may be in any form suitable for use in the article, including, particles, fibers, flakes, spheres, and the like. The swellable material may be sealed within or between one or more layers of liquid permeable materials such as, for example, sheets of cellulosic tissue or meltblown. By way of non-limiting example, suitable superabsorbent materials and methods of incorporating the same into materials and/or pouches are described in U.S. Pat. Nos. 4,646,510, 5,458, 592 and 6,162,961, the expandable or swellable material may comprise an absorbent, swellable foam.

In certain embodiments the cleansing article may include multiple core members so as to improve and/or provide multiple distinct functions of the same. By way of example, the cleansing article may include a first core member comprising a resiliently-deformable porous layer capable of improving foam generation and handleability. In addition, the cleansing article may further include a second core member comprising a porous layer impregnated with a cleaning formulation. Thus, after wetting the article, a user's squeezing and releasing of the article causes the cleaning formulation to transfer to outer members and for air to be draw into and pushed throughout the layers of the article thereby aiding in the development of a rich foamy lather.

In a further aspect, one or more layers of the article may include one or more cleaning or exfoliating agents to assist with the desired function of the article. For example, the first or second outer member, or the core, may be impregnated with or have applied thereto a cleaning formulation. Skin cleaning formulations are well-known in the art and may include one or more of the following ingredients: cleansing and/or foaming (lathering) surfactants, detergents, builders, foam stabilizers, astringents, essential oils, plant extracts, humectants, moisturizing agents, buffering agents, chelating agents, anti-microbial agents, pigments, colorants, fragrances, and so forth. Foam generating surfactants, i.e. lathering surfactants, are widely known and used and are particularly well suited for use in cleansing formulations included in the cleansing article of the present invention. By way of example, suitable foam generating surfactants include, but are not limited to, glucosides (e.g. alkyl glucosides, alkyl polyglucosides, etc.), betaines (e.g. cetyl betaine, cetyl dimethyl betaine, cocamidopropyl betaine, lauryl dimethyl carboxymethyl betaine, etc.), alkyl and alkyl ether sulfates (e.g. sodium lauryl sulfate sodium, sodium laureth sulfate, cetyl sulfate, etc.), alkoxylated fatty acid esters, sultaines (e.g. cocamidopropyl hydroxysultaine, etc.), amine oxides (e.g. lauramine oxide, cocoamine oxide, etc.), alkyl isethionates (e.g. sodium cocoyl isethionate, sodium lauroyl isethionate, etc.), and so forth. Further, non-limiting examples of suitable cleaning formulations are described in U.S. Pat. No. 6,806,213 and US Publication Nos. 2003/ 207632 and US2005/136531. Desirably, one or more of the interior layers, such as the first outer member or a core layer, includes an effective amount of a lathering surfactant to enable the formation of a rich lather upon repeatedly pressing and releasing the wet article. As but one specific example, the cleaning formulation may include a combination of the following ingredients: decyl glucoside, glycerin, cocamidopropyl betaine, PEG-7 glyceryl cocoate, tocopheryl acetate, malic acid, and a cosmetically acceptable preservative.

The article, and cleaning formulation, may be provided in either a moist or dry form as desired. By way of non-limiting example, cleaning formulations may be applied to a core layer by dipping, spraying, printing (e.g. flexographic, rotogravure, offset, etc.), gravure coating, flexographic coating, slot coating, foam application, and so forth. Often it will be desirable to apply the cleaning formulation in aqueous form and thereafter remove excess water by hot air drying or other methods in order to achieve either a dry product or a moist product with higher percentages of functional ingredients. In alternative embodiments, it is noted that a cleansing formulation may be separately and/or additionally impregnated in or applied to one or more of the other layers including the first outer member or the second outer member. In certain embodiments, it will be desirable for the article to comprise, based upon its dry weight, between about 1 and 500 percent by weight of a cleaning formulation and/or a lathering surfactant. In still further embodiments, it will be desirable for the article to comprise between about 1 and about 250 percent, and still more desirably between about 5 and about 100 percent, of a cleaning formulation and/or lathering surfactant (based upon the dry weight of the article).

In a further aspect, any one or more layers in the cleansing article may optionally include one or more additives or topical agents in order to modify or improve its inherent hydrophilic and/or hydrophobic character. Often it will be desirable to increase the wettability or hydrophilic characters of a layer such as, for example, by the application or inclusion of wetting agents and/or surfactants. As a further option, one or more layers may include pigments, opacifying agents, softening agents, particulates, fragrances and so forth as desired to impart or improve one or more physical or aesthetic attributes. The materials comprising the various layers may also optionally be physically treated as desired to enhance or improve additional characteristics such as, for example, hand (feel), appearance, durability, and so forth. In this regard, examples of commonly employed treatments include, but are not limited to, embossing, stretching, creping, printing, needling and so forth.

TEST METHODS

Air Permeability

Air permeability, which expresses the permeability of a material in terms of cubic feet per minute of air through a square foot of area of a surface of the material at a pressure drop of 100 Pa, was determined in accordance with ISO 9237:1995. The measurement was taken using a TEXTEST FX 3300 (TEXTEST AG, Switzerland) fitted with a 20 cm$^2$ head at a test pressure of 100 Pa.

Surface Properties

The surface properties of samples were measured on KES Surface Tester (Model KE-SE, Kato Tech Co., Ltd., Kyoto, Japan). For each sample the coefficient of friction and/or surface smoothness was measured according to the Kawabata Test Procedures with samples tested along MD and CD and on both sides for five repeats with a sample size of 10 cm×10 cm. Care was taken to avoid folding, wrinkling, stressing, or otherwise handling the samples in a way that would deform the sample. Samples were tested using a multi-wire probe of 10 mm×10 mm consisting of 20 piano wires of 0.5 mm in diameter each with a contact force of 25 grams. The test speed was set at 1 mm/s. The sensor was set at "H" and FRIC was set at "DT". The data was acquired using KES-FB System Measurement Program KES-FB System Ver 7.09 E for Win98/2000/XP (commercially available from Kato Tech Co., Ltd., Kyoto, Japan). The selection in the program was "KES-SE Friction Measurement".

KES Surface Tester determined the coefficient of friction (MIU) and mean deviation of MIU (MMD), where higher values of MIU indicate more drag on the sample surface and higher values of MMD indicate more variation or less uniformity on the sample surface.

The values MIU and MMD are defined by:

$$MIU(\bar{\mu})=1/X\int_0^x \mu\, dx$$

$$MMD=1/X\int_0^x |\mu-\bar{\mu}|\, dx$$

where
µ=friction force divided by compression force
$\bar{\mu}$=mean value of µ
x=displacement of the probe on the surface of specimen, cm
X=maximum travel used in the calculation, 2 cm The top surface of each product sample was tested five times and resulting MMD and MIU values averaged and reported as coefficient of friction (COF) and surface smoothness.

Image Analysis

Image analysis of samples was carried out using a Leica Microsystems QWIN Pro Image Analysis system (Version 3.5.1, commercially available from Leica Microsystems, Heerbrugg, Switzerland) under the optical axis of a 20 mm Nikon AF lens with an f-stop setting of 4. The Nikon lens was attached to the Leica DFC 310 FX camera using a c-mount adaptor. Two-dimensional coverage, spacing, density and sizing data were acquired via the QUIPS algorithm "Coverage, Size & Spacing Distribution-1." The optical configuration is described in the algorithm.

Three-dimensional surface maps and height profiles were acquired using a Leica 3D stereo microscope with Mountains surface topography software. Z-height image slice focusing was performed at 30X magnification, while image slices (8) were acquired at 7.8× magnification.

EXAMPLES

Several different exfoliating products were prepared to evaluate the effect of basesheet, printing material and patterns on surface properties and exfoliation. The composition of each of the products is summarized in Table 2, below. Two different basesheets were evaluated. Both basesheets were bonded carded webs comprising bi-component fibers (polyethylene and polypropylene) having a basis weight of about 57 grams per square meter (gsm). The basesheets had two different calipers—a caliper of about 1.15 mm (Basesheet A) and a caliper of about 1.27 mm (Basesheet B). Both basesheets are commercially available from Precision Customer Coating, Totowa, N.J. The desired patterns were printed on the basesheets by screen printing a paste that expands under heating by virtue of a puffing agent contained therein. The paste used to produce the inventive samples is marketed as Altoma Puff Paste (Bolger & O'Hearn, Inc., Fall River, Mass.). The webs were printed using conventional screen printing technology using a printing screen imparted with a pattern. The screen pattern was substantially similar to that illustrated in FIG. 8A, with the number of dots, dot size and dot spacing varied as provided in Table 2, below. After printing webs were cured by heating in an oven at about 310° F. After curing the products were subjected to analysis as described in the Test Methods section above, the results of which are summarized in Table 3, below.

TABLE 2

| Trail Code | Basesheet | Dots per Pattern | Pattern Dot Diameter (mm) |
|---|---|---|---|
| 1 | A | 13 | 0.6 |
| 2 | A | 12 | 0.6 |
| 3 | B | 13 | 0.6 |
| 4 | B | 13 | 0.4 |
| 5 | B | 12 | 0.6 |

TABLE 3

| Trail Code | % Surface Area Printed | Measured Diameter (mm) | Average Dot Height (µm) | Approx. Dot Volume (mm$^3$) | Coefficient of Friction | Surface Smoothness |
|---|---|---|---|---|---|---|
| 1 | 10.4 | 0.94 | 611 | 0.312 | 1.154 | 0.059 |
| 2 | 8.4 | 0.95 | 566 | 0.275 | 0.805 | 0.045 |
| 3 | 9.2 | 1.00 | 378 | 0.295 | 0.757 | 0.047 |
| 4 | 12.7 | 1.20 | 506 | 0.119 | 0.670 | 0.057 |
| 5 | 9.7 | 0.91 | 612 | 0.064 | 1.284 | 0.090 |

While the inventive textured cleansing articles have been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto and the following embodiments:

In a first embodiment the present invention provides a textured cleansing article comprising: a first member comprising a nonwoven web having an outer and an inner surface, a plurality of non-hollow protuberances disposed on the outer surface, the first member having a permeability greater than 500 cfm and a coefficient of friction greater than 0.50; a second member comprising a nonwoven web having an outer and an inner surface and a coefficient of friction less than 0.50; and a core disposed between the first and the second members.

In a second embodiment the present invention provides the textured cleansing article of the first embodiment wherein the plurality of protuberance have an average height greater than about 250 µm, such as from about 250 to about 1,000 µm.

In a third embodiment the present invention provides the textured cleansing article of the first or second embodiments wherein the plurality of protuberances are disposed on the first side at a density greater than about 100,000 protuberances/m$^2$ and still more preferably greater than about 120,000 protuberances/m$^2$, such as from about 100,000 to about 200,000 protuberances/m$^2$ and more preferably from about 120,000 to about 170,000 protuberances/m$^2$.

In a fourth embodiment the present invention provides the textured cleansing article of any one of the first through third embodiments wherein the protuberances are disposed on the first side in a non-random pattern comprising a plurality of circles.

In a fifth embodiment the present invention provides the textured cleansing article of any one of the first through fourth embodiments wherein the core is a porous open cell foam and further comprises a cleansing formulation.

In a sixth embodiment the present invention provides the textured cleansing article of any one of the first through fifth embodiments wherein the second member comprises a fluid-entangled laminate web having an outer and an inner surface, the outer surface of the web having a plurality of hollow projections.

In a seventh embodiment the present invention provides the textured cleansing article of any one of the first through sixth embodiments wherein the plurality of non-hollow protuberance have an average height from about 300 to about 650 μm.

In an eighth embodiment the present invention provides the textured cleansing article of any one of the first through seventh embodiments wherein the first outer surface has a coefficient of friction from preferably from about 0.75 to about 1.20 and the second outer surface has a coefficient of friction from about 0.35 to about 0.45.

In a ninth embodiment the present invention provides the textured cleansing article of any one of the first through eighth embodiments wherein the plurality of non-hollow protuberances have a substantially semi-spherical shape having an average volume from about 0.50 to about 0.70 mm$^3$.

In a tenth embodiment the present invention provides the textured cleansing article of any one of the first through ninth embodiments wherein the plurality of non-hollow protuberances have an average diameter from about 500 to about 2,000 μm.

In an eleventh embodiment the present invention provides the textured cleansing article of any one of the first through tenth embodiments wherein the plurality of non-hollow protuberances are printed in a non-random pattern comprising a plurality of circles, each circle comprising from about 8 to about 15 protuberances and having a diameter from about 5.00 to about 15.0 mm.

In a twelfth embodiment the present invention provides the textured cleansing article of any one of the first through eleventh embodiments wherein the plurality of non-hollow protuberances are printed in a non-random pattern and cover at least about 8 percent, such as from about 8 to about 12 percent, of the surface area of the outer surface of the first member.

What is claimed is:

1. A cleansing article comprising:
    a) a first member comprising a nonwoven web having a first and a second side and a plurality of non-hollow polymeric protuberances disposed on the first side thereof, the first side forming the first outer surface of the cleansing article;
    b) a second member comprising a nonwoven web having a first and a second side, the first side having a plurality of hollow projections substantially surrounded by a landing, the land areas lying in a first plane and the projections terminating at distal ends lying in a second plane, the first and second planes spaced apart a vertical distance from about 0.5 to about 1.5 mm, wherein the first side forms the second outer surface of the cleansing article; and
    c) a core disposed between the first and the second members;
    wherein the first outer surface has a coefficient of friction greater than 0.50 and the second outer surface has a coefficient of friction less than 0.50.

2. The cleansing article of claim 1 wherein the plurality of polymeric protuberances have an average height from about 300 to about 650 μm.

3. The cleansing article of claim 1 wherein the first outer surface has a coefficient of friction from about 0.75 to about 1.20 and the second outer surface has a coefficient of friction from about 0.35 to about 0.45.

4. The cleansing article of claim 1 wherein the plurality of polymeric protuberances have a substantially semi-spherical shape having an average volume from about 0.50 to about 0.70 mm$^3$.

5. The cleansing article of claim 1 wherein the first outer surface has a surface area and the plurality of polymeric protuberances cover from about 5.0 to about 15.0 percent of the surface area.

6. The cleansing article of claim 1 wherein the first member has a permeability of 500 cfm or greater and the second member has a permeability less than 500 cfm.

* * * * *